US 8,957,393 B2

(12) United States Patent
Iwata

(10) Patent No.: US 8,957,393 B2
(45) Date of Patent: *Feb. 17, 2015

(54) PARTICLE BEAM IRRADIATION APPARATUS AND PARTICLE BEAM THERAPY SYSTEM

(71) Applicant: Mitsubishi Electric Corporation, Chiyoda-ku (JP)

(72) Inventor: Takaaki Iwata, Chiyoda-ku (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/451,481

(22) Filed: Aug. 5, 2014

(65) Prior Publication Data

US 2014/0350324 A1    Nov. 27, 2014

Related U.S. Application Data

(60) Division of application No. 13/963,000, filed on Aug. 9, 2013, now Pat. No. 8,829,466, which is a continuation of application No. 13/055,479, filed as application No. PCT/JP2010/055863 on Mar. 31, 2010, now Pat. No. 8,592,778.

(51) Int. Cl.
*A61N 5/10* (2006.01)
*H01J 37/147* (2006.01)
(Continued)

(52) U.S. Cl.
CPC ............... *H01J 37/147* (2013.01); *G21K 5/04* (2013.01); *A61N 5/1077* (2013.01); *G06N 3/02* (2013.01); *H01J 2237/0473* (2013.01)
USPC ........................ 250/398; 250/492.3

(58) Field of Classification Search
CPC ....... A61N 5/10; A61N 5/103; A61N 5/1048; A61N 5/1064; A61N 5/1075; H01J 37/04; H01J 37/147; H01J 37/1472; H01J 37/1474; H01J 37/1475; H01J 37/302
USPC ............... 250/396 R–398, 400, 492.1, 492.3
See application file for complete search history.

(56) References Cited

U.S. PATENT DOCUMENTS 6,614,038 B1 * 9/2003 Brand et al. ............... 250/492.3
6,745,072 B1 * 6/2004 Badura et al. ................ 607/2
(Continued)

FOREIGN PATENT DOCUMENTS

JP    2005-296162 A    10/2005
JP    2007-132902 A    5/2007
(Continued)

OTHER PUBLICATIONS

International Search Report (PCT/ISA/210) mailed on Apr. 27, 2010, by the Japanese Patent Office as the International Searching Authority for International Application No. PCT/JP2010/055863.
(Continued)

*Primary Examiner* — Jack Berman
*Assistant Examiner* — David E Smith
(74) *Attorney, Agent, or Firm* — Buchanan Ingersoll & Rooney PC

(57) ABSTRACT

A scanning power source that outputs the excitation current for a scanning electromagnet and an irradiation control apparatus that controls the scanning power source; the irradiation control apparatus is provided with a scanning electromagnet command value learning generator that evaluates the result of a run-through, which is a series of irradiation operations through a command value for the excitation current outputted from the scanning power source, that updates the command value for the excitation current, when the result of the evaluation does not satisfy a predetermined condition, so as to perform the run-through, and that outputs to the scanning power source the command value for the excitation current such that its evaluation result has satisfied the predetermined condition.

20 Claims, 8 Drawing Sheets

(51) Int. Cl.
*G21K 5/04* (2006.01)
*G06N 3/02* (2006.01)

(56) References Cited

U.S. PATENT DOCUMENTS

| | | |
|---|---|---|
| 6,859,741 B2 | 2/2005 | Haberer et al. |
| 6,922,700 B1 | 7/2005 | Aggarwal et al. |
| 7,060,997 B2 * | 6/2006 | Norimine et al. .......... 250/505.1 |
| 7,838,855 B2 | 11/2010 | Fujii et al. |
| 2002/0174079 A1 * | 11/2002 | Mathias et al. ................. 706/15 |
| 2009/0039256 A1 * | 2/2009 | Fujii et al. ..................... 250/306 |
| 2011/0116200 A1 | 5/2011 | Steiner |
| 2013/0345490 A1 * | 12/2013 | Iwata ............................... 600/1 |

FOREIGN PATENT DOCUMENTS

| | | | |
|---|---|---|---|
| JP | 2007132902 A | * | 5/2007 |
| JP | 2008-272139 A | | 11/2008 |
| JP | 2009-347 A | | 1/2009 |
| JP | 2009-39219 A | | 2/2009 |
| WO | WO 2009/130002 A1 | | 10/2009 |

OTHER PUBLICATIONS

Jul. 29, 2013 Taiwanese Office Action issued in Taiwanese Patent Application No. 10220998160.

\* cited by examiner

FIG. 4

| Bx \ By | $(B_0, B_1)$ | $(B_1, B_2)$ | ... | $(B_{m-1}, B_m)$ |
|---|---|---|---|---|
| $(B_0, B_1)$ | $S_{0,0}$ | $S_{0,1}$ | ... | $S_{0,m-1}$ |
| $(B_1, B_2)$ | $S_{1,0}$ | $S_{1,1}$ | | |
| ⋮ | ⋮ | | ⋱ | |
| $(B_{m-1}, B_m)$ | $S_{m-1,0}$ | | | $S_{m-1,m-1}$ |

FIG. 5

| de | score |
|---|---|
| $+4\Delta d \leq de$ | −200 |
| $+3\Delta d \leq de < +4\Delta d$ | −100 |
| $+2\Delta d \leq de < +3\Delta d$ | −50 |
| $+\Delta d \leq de < +2\Delta d$ | −20 |
| $-\Delta d \leq de < +\Delta d$ | 0 |
| $-2\Delta d \leq de < -\Delta d$ | −10 |
| $-3\Delta d \leq de < -2\Delta d$ | −25 |
| $-4\Delta d \leq de < -3\Delta d$ | −50 |
| $de < -4\Delta d$ | −100 |

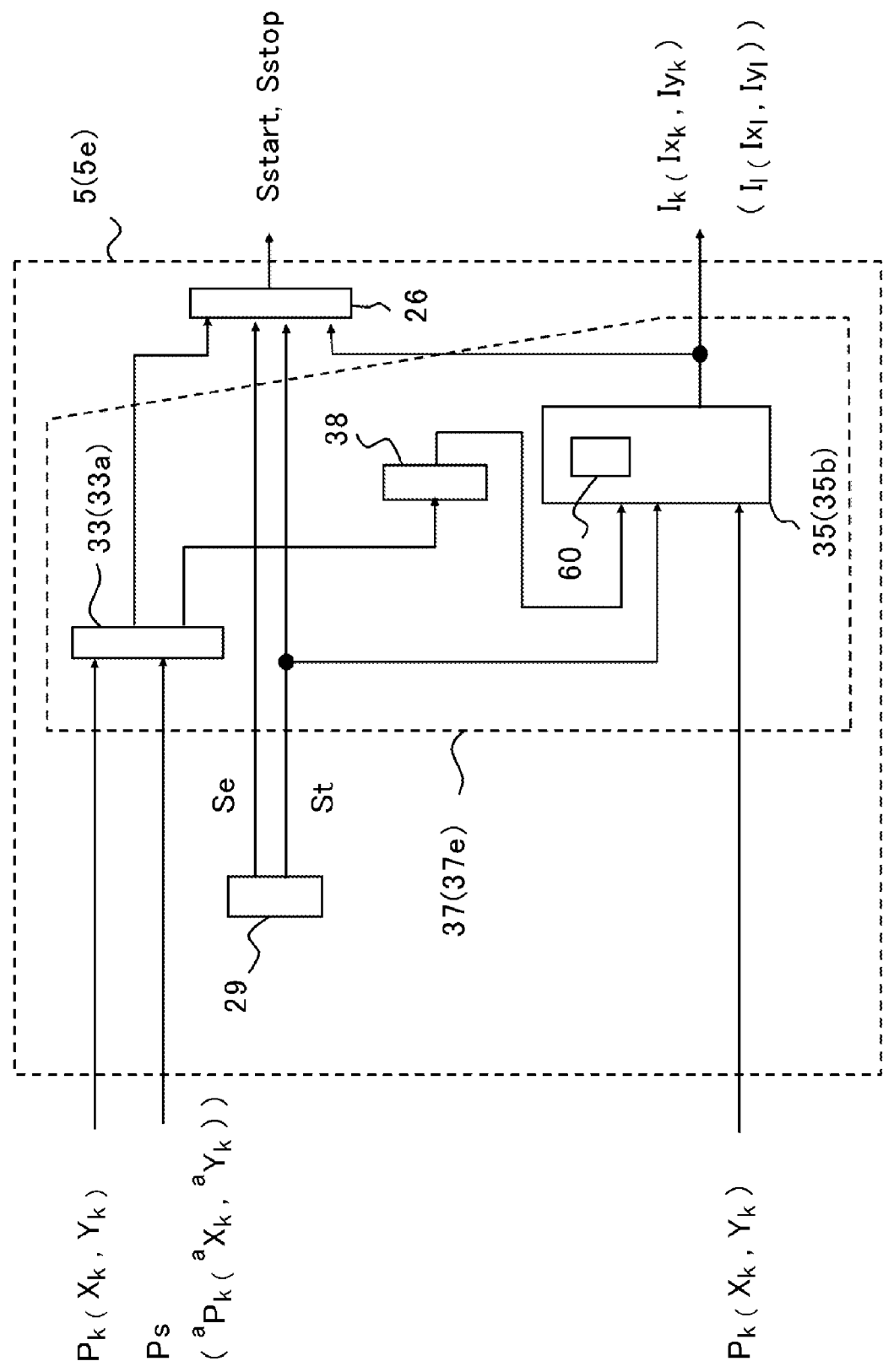

PARTICLE BEAM IRRADIATION APPARATUS AND PARTICLE BEAM THERAPY SYSTEM

TECHNICAL FIELD

The present invention relates to a particle beam therapy system utilized in the medical field and R&Ds, and particularly to a particle beam irradiation apparatus and a particle beam therapy system of a scanning type such as a raster-scanning type.

BACKGROUND ART

In general, a particle beam therapy system is provided with a beam generation apparatus that generates a charged particle beam; an accelerator that is connected with the beam generation apparatus and accelerates a generated charged particle beam; a beam transport system that transports a charged particle beam that is accelerated by the accelerator so as to gain predetermined energy and then emitted; and a particle beam irradiation apparatus, disposed at the downstream side of the beam transport system, for irradiating a charged particle beam onto an irradiation subject. Particle beam irradiation apparatuses are roughly divided into apparatuses utilizing a broad irradiation method in which a charged particle beam is enlarged in a dispersion manner by a scatterer, and the shape of the enlarged charged particle beam is made to coincide with the shape of an irradiation subject in order to form an irradiation field; and apparatuses utilizing a scanning irradiation method (the spot-scanning method, the raster-scanning method, and the like) in which an irradiation field is formed by performing scanning with a thin, pencil-like beam in such a way that the scanning area coincides with the shape of an irradiation subject.

The spot-scanning method is, briefly speaking, a method of forming an irradiation field by irradiating a particle beam in a small spot shape as in pointillism. In other words, the cycle consisting of supply of a beam (dotting), stoppage of a beam, and movement is repeated. The spot-scanning method is a high-flexibility irradiation method in which an irradiation dose can be changed in accordance with a spot position, and it has been attracting a large attention in recent years.

The raster-scanning method is, briefly speaking, a method of forming an irradiation field by keeping a particle beam irradiated as in single-stroke painting. That is to say, it is a method of continuously irradiating a beam and making the beam move at a constant speed within a region where the target dose is constant. It has an advantage in that, because it is not required to repeat the cycle consisting of supply of a beam and stoppage of a beam, the therapy takes only a short time.

There has been proposed an irradiation method that is intermediate between the spot-scanning method and the raster-scanning method. As in the raster-scanning method, a beam is kept irradiated, and as in the spot-scanning method, the beam spot position moves among the spot positions one after another. The intermediate irradiation method intends to acquire the advantages of both the spot-scanning method and the raster-scanning method. In this description, the foregoing intermediate irradiation method will be referred to as a hybrid scanning method.

In the broad irradiation method, an irradiation field that coincides with the shape of a diseased site is formed by use of a collimator or a bolus. The broad irradiation method is a most universally utilized and superior irradiation method where an irradiation field that coincides with the shape of a diseased site is formed so as to prevent unnecessary irradiation onto a normal tissue. However, it is required to create a bolus for each patient or to change the shape of a collimator in accordance with a diseased site.

In contrast, the scanning irradiation method is a high-flexibility irradiation method where, for example, neither collimator nor bolus is required. However, because these components for preventing irradiation onto not a diseased site but a normal tissue are not utilized, there is required a positional accuracy of beam irradiation that is the same as or higher than that of the broad irradiation method.

With regard to a particle beam therapy system, there have been implemented various inventions that raise the accuracies of an irradiation position and an irradiation dose. Patent Document 1 discloses an invention, stated below, that has an objective of providing a particle beam therapy system capable of accurately irradiating a diseased site. In the invention disclosed in Patent Document 1, there are stored, in a memory device, the amount of charged particle beams scanned by a scanning apparatus and the position of a charged particle beam detected by a beam position detector while the charged particle beam is emitted; then, by utilizing the stored scanning amount and the beam position, the scanning amount of the beam scanning apparatus is set by a control apparatus, in accordance with the beam position based on information about a treatment plan. The relationship between the scanning amount and the beam position, which is obtained by actually performing irradiation, is stored in the memory device; therefore, accurate irradiation onto a diseased site can be expected.

Patent Document 2 discloses an invention, stated below, that has an objective of providing a particle beam therapy system capable of ensuring high safety and emitting a charged particle beam in a highly accurate manner. In the invention disclosed in Patent Document 2, a charged particle beam emitted from a charged particle beam generation apparatus is supplied to a scanning electromagnet that performs irradiation on an irradiation plane perpendicular to the traveling direction of the beam; then, the amount of charged particle beams emitted from the charged particle beam generation apparatus is controlled based on the position and the dose, on the irradiation plane, of the charged particle beam that passes through the scanning electromagnet. Specifically, the supply of a charged particle beam to the region, among a plurality of regions formed by dividing the irradiation plane, where a target dose has been achieved is stopped, and charge particle beams are supplied to the other regions where the target dose has not been achieved. As described above, the irradiation dose in each of the regions is compared with the target dose, and the emission amount of a charged particle beam is on/off-controlled (supplied/not supplied), so that high safety is expected.

With regard to a problem that hysteresis characteristics existing in the relationship between the current and the magnetic field of a scanning electromagnet deteriorates the accuracy of a beam irradiation position, Patent Document 3 discloses an invention stated below. The invention disclosed in Patent Document 3 has a first calculation means that calculates, without taking the effect of the hysteresis into account, the current value of a scanning electromagnet in accordance with the beam irradiation position based on an irradiation plan; and a second calculation means that performs, taking the effect of the hysteresis into account, a correction calculation of the current value of the scanning electromagnet calculated by the first calculation means. An irradiation control apparatus controls the current of the scanning electromagnet, based on the result of the calculation by the second calculation means. As described above, a correction calculation is performed by the second calculation means so as to eliminate the effect of the hysteresis, i.e., the second calculation means has a mathematical model where the hysteresis characteristics are represented, so that the improvement of the accuracy of a beam irradiation position is expected through the calculation.

PRIOR ART REFERENCE

Patent Document

[Patent Document 1] Japanese Patent Application Laid-Open No. 2005-296162
[Patent Document 2] Japanese Patent Application Laid-Open No. 2008-272139
[Patent Document 3] Japanese Patent Application Laid-Open No. 2007-132902

DISCLOSURE OF THE INVENTION

Problem(S) to be Solved by the Invention

In the invention disclosed in Patent Document 1, a transformation table is created based on actual data on the scanning amount and the position, of a charged particle beam, which are obtained through actual irradiation, and by utilizing this transformation table, the setting current value of a scanning electromagnet is calculated.

However, in fact, as disclosed in Patent Document 3, because there exist hysteresis characteristics between the current and the magnetic field of the scanning electromagnet, the magnetic field at a time when the current value increases differs from the magnetic field at a time when the current decreases. That is to say, even though the current value of the scanning electromagnet at an instant is obtained, the accurate value of the magnetic field cannot be determined only through the information. Accordingly, in the invention disclosed in Patent Document 1, there has been a problem that, due to the effect of the hysteresis of the electromagnet, accurate irradiation of a diseased site cannot be performed.

In the invention disclosed in Patent Document 2, the emission amount of a charged particle beam is on/off controlled (supplied/not supplied) in such a way that the irradiation dose at each of defined regions becomes a target dose.

However, the plurality of regions, formed on an irradiation plane through division, which are described in the invention disclosed in Patent Document 2 are regions (excitation regions) in the excitation current space defined by the range of the excitation current of the corresponding scanning electromagnet; thus, the excitation region does not coincide with the region (irradiation region) in the actual irradiation space. That is because the excitation region and the irradiation region do not correspond to each other on a one-to-one basis unless the hysteresis of the scanning electromagnet is considered. Accordingly, even in an apparatus or a method where the irradiation dose for each excitation region is administered so as to raise the safety, there is not demonstrated the effect of administrating the dose in a small region, unless the effect of the hysteresis of the scanning electromagnet is eliminated. That is to say, there has been a problem that the hysteresis of the scanning electromagnet deteriorates the accuracy of the beam irradiation position.

In the invention disclosed in Patent Document 3, a mathematical hysteresis model is made in the inside of a calculation means, and through calculation, the current value of a scanning electromagnet is corrected.

However, even though the hysteresis is considered, a number of problems still exist in the invention disclosed in Patent Document 3. The first problem is that it is practically rather difficult to accurately correct the hysteresis characteristic by use of a calculation method. For example, the mode of the curve representing the hysteresis characteristic between the current and the magnetic field varies depending on not only the amplitude of the input (current) but also the speed of changing the input (current) or the changing pattern. In order to express the complicated hysteresis phenomenon by a calculation method, i.e., a mathematical model, studies and contrivances have been made for a long time in many fields; however, it is practically difficult to achieve it. The second problem is found in the method of detecting a beam irradiation position. As the invention disclosed in Patent Document 3, most of conventional methods try to detect a beam irradiation position by only a single beam position monitor or a plurality of beam position monitors. A beam position monitor does not learn a beam irradiation position by the time a charged particle beam is emitted. Accordingly, when a beam is way off the target and is irradiated onto a normal tissue or the like, all can be done is to stop the beam; thus, there has been a problem that the beam irradiation position cannot be controlled to fall on a right irradiation position onto which the beam should be emitted.

The present invention has been implemented in order to solve the foregoing problems; the objective thereof is to eliminate the effect of the hysteresis of a scanning electromagnet so that, in the raster scanning or the hybrid scanning, there is obtained a particle beam irradiation apparatus that realizes high-accuracy beam irradiation.

Means for Solving the Problems

There are provided a scanning power source that outputs an excitation current for a scanning electromagnet and an irradiation control apparatus that controls the scanning power source. The irradiation control apparatus has a scanning electromagnet command value learning generator that evaluates the result of a run-through, which is a series of irradiation operations through a command value for the excitation current outputted from the scanning power source, that updates the command value for the excitation current, when the result of the evaluation does not satisfy a predetermined condition, so as to perform the run-through, and that outputs to the scanning power source the command value for the excitation current such that its evaluation result has satisfied the predetermined condition.

Advantage of the Invention

In the particle beam irradiation apparatus according to the present invention, based on the result of the run-through, the scanning electromagnet command value learning generator can suitably learn the excitation-current command value outputted to the scanning power source; thus, the effect of the hysteresis of the scanning electromagnet is eliminated, so that high-accuracy beam irradiation can be realized in the raster-scanning and the hybrid scanning.

BRIEF DESCRIPTION OF THE DRAWINGS

FIG. 4 is a table representing a plurality of regions defined in a magnetic-field space;

FIG. 5 represents an example of score table at a time when learning irradiation is performed;

FIG. 9 is a block diagram of an irradiation control apparatus according to Embodiment 3 of the present invention.

BEST MODE FOR CARRYING OUT THE INVENTION

Embodiment 1

Figure 1:
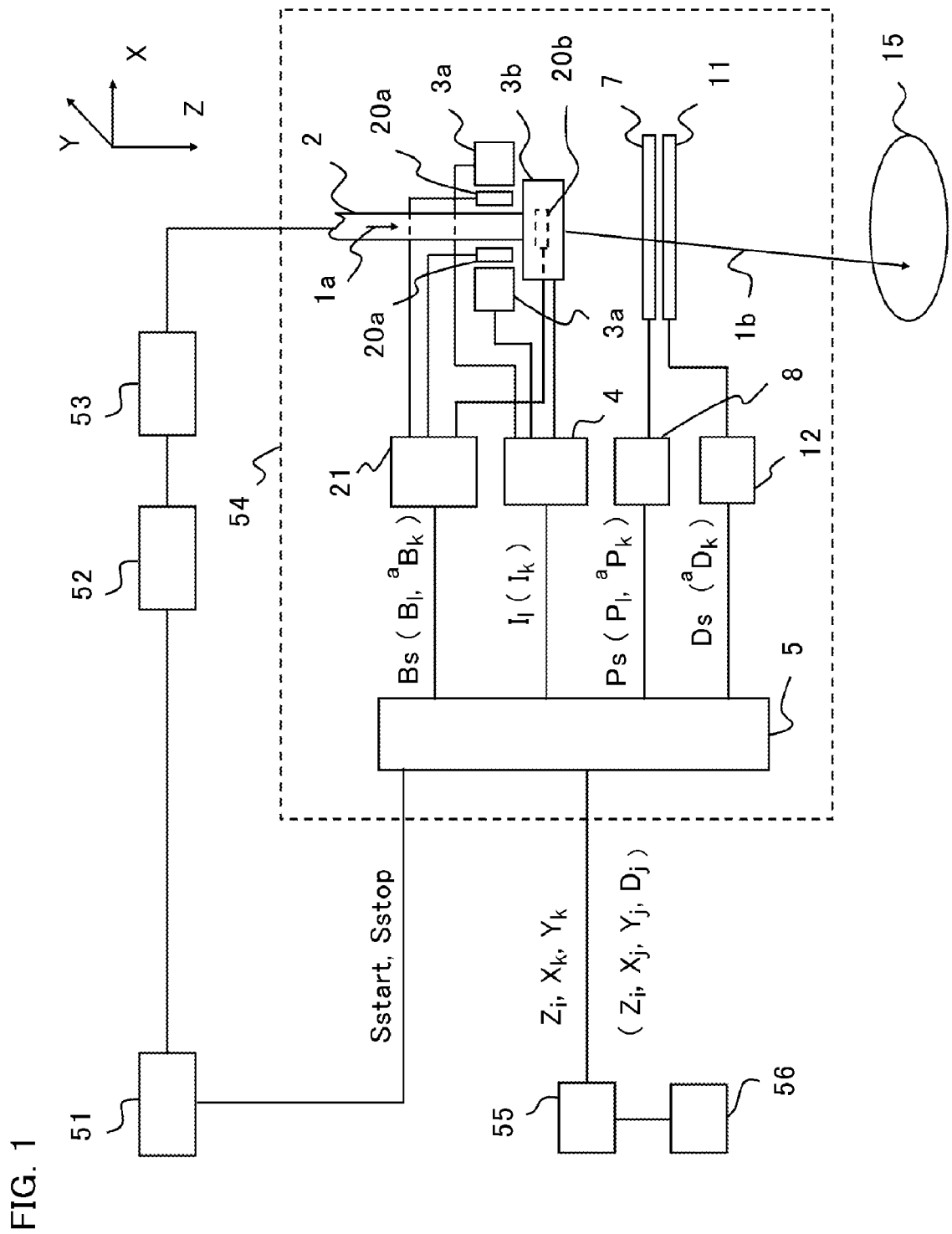
FIG. 1 is a schematic block diagram illustrating a particle beam therapy system according to Embodiment 1 of the present invention.

FIG. 1 is a schematic block diagram illustrating a particle beam therapy system according to Embodiment 1 of the present invention. The particle beam therapy system includes a beam generation apparatus 51, an accelerator 52, a beam transport apparatus 53, a particle beam irradiation apparatus 54, a treatment plan apparatus 55, and a data server 56. The treatment planning apparatus 55 can also be provided as not a component of the particle beam therapy system but an independent apparatus. The beam generation apparatus 51 generates a charged particle beam by accelerating charged particles generated in an ion source. The accelerator 52 is connected with the beam generation apparatus 51 and accelerates a generated charged particle beam. The beam transport apparatus 53 transports a charged particle beam that is accelerated by the accelerator 52 so as to gain predetermined energy and then emitted. The particle beam irradiation apparatus 54 is disposed at the downstream side of the beam transport system 53 and irradiates a charged particle beam onto an irradiation subject 15.

Based on the 3-dimensional data on the diseased site 15, which is an irradiation subject, the treatment planning apparatus 55 can make plans for several therapies such as irradiation conditions so as to simulate the particle beam therapy. In the treatment planning apparatus 55, the treatment plan that has been finally selected by a doctor who carries out the particle beam therapy is converted into codes for driving the particle beam therapy system. For example, in the case of the spot-scanning method, the code for driving the particle beam therapy system means the coordinates $X_j, Y_j$ (the subscript "j" signifies a spot number) of a spot for each irradiation layer $Z_i$ (the subscript "I" signifies a layer number) and a target dose $D_j$ to be irradiated onto the spot; in the case of the raster-scanning method, the code means time-series data and the like obtained by representing an irradiation orbit for each irradiation layer $Z_i$ by an irradiation position $X_k, Y_k$ (the subscript "k" signifies a sequence number) for each sampling period. Here, the reason why the wording "a target dose $D_j$ to be irradiated onto the spot" has been utilized is that, due to the characteristics of the Bragg peak, the irradiation onto a lower layer affects the upper layer; the foregoing target dose does not signify the target dose to be required at the spot. The data server 56 stores treatment plan data that is created by the treatment plan apparatus 55 for each patient and codes for driving the driving the particle beam therapy system.

The particle beam irradiation apparatus 54 is provided with a beam transport duct 2 for transporting an incident charged particle beam 1a injected by the beam transport apparatus 53; scanning electromagnets 3a and 3b that scan the incident charged particle beam 1a in the X direction and the Y direction, respectively, which are directions perpendicular to the incident charged particle beam 1a; magnetic-field sensors 20a and 20b that detect magnetic fields generated by the scanning electromagnets 3a and 3b; a magnetic-field data converter 21; a beam position monitor 7; a position data converter 8; a dose monitor 11; a dose data converter 12; an irradiation control apparatus 5; and a scanning power source 4. The magnetic-field sensors 20a and 20b are, for example, magnetic-field sensors having a pickup coil. As illustrated in FIG. 1, the traveling direction of the incident charged particle beam 1a is the Z direction.

The scanning electromagnet 3a is an X direction scanning electromagnet that performs X-direction scanning with the incident charged particle beam 1a; the scanning electromagnet 3b is a Y direction scanning electromagnet that performs Y-direction scanning with the incident charged particle beam 1a. The magnetic-field sensor 20a is an X direction magnetic-field sensor that detects an X direction magnetic field; the magnetic-field sensor 20b is a Y direction magnetic-field sensor that detects a Y direction magnetic field. The magnetic-field data converter 21 converts an electric signal of a sensor, which indicates a magnetic field detected by the magnetic-field sensors 20a and 20b, into a digital-data measured magnetic field Bs. The beam position monitor 7 detects the passing position of an outgoing charged particle beam 1b that has been deflected by the scanning electromagnets 3a and 3b. The position data converter 8 calculates the irradiation position on an irradiation layer based on an electric signal of a sensor, which indicates the passing position detected by the beam position monitor 7, and generates digital-data measured irradiation position coordinates Ps. The dose monitor 11 detects the dose of the outgoing charged particle beam 1b. The dose data converter 12 converts an electric signal of a sensor, which indicates a dose detected by the dose monitor 11, into digital-data measured dose Ds.

The irradiation control apparatus 5 outputs excitation-current command currents $Ix_k, Iy_k$, which are excitation-current command values for the scanning power source 4, so as to control the irradiation position on each irradiation layer $Z_i$. The scanning power source 4 outputs an excitation current for actually driving the scanning electromagnets 3a and 3b, based on the command currents $Ix_k$ and $Iy_k$ outputted from the irradiation control apparatus 5.

Figure 2:
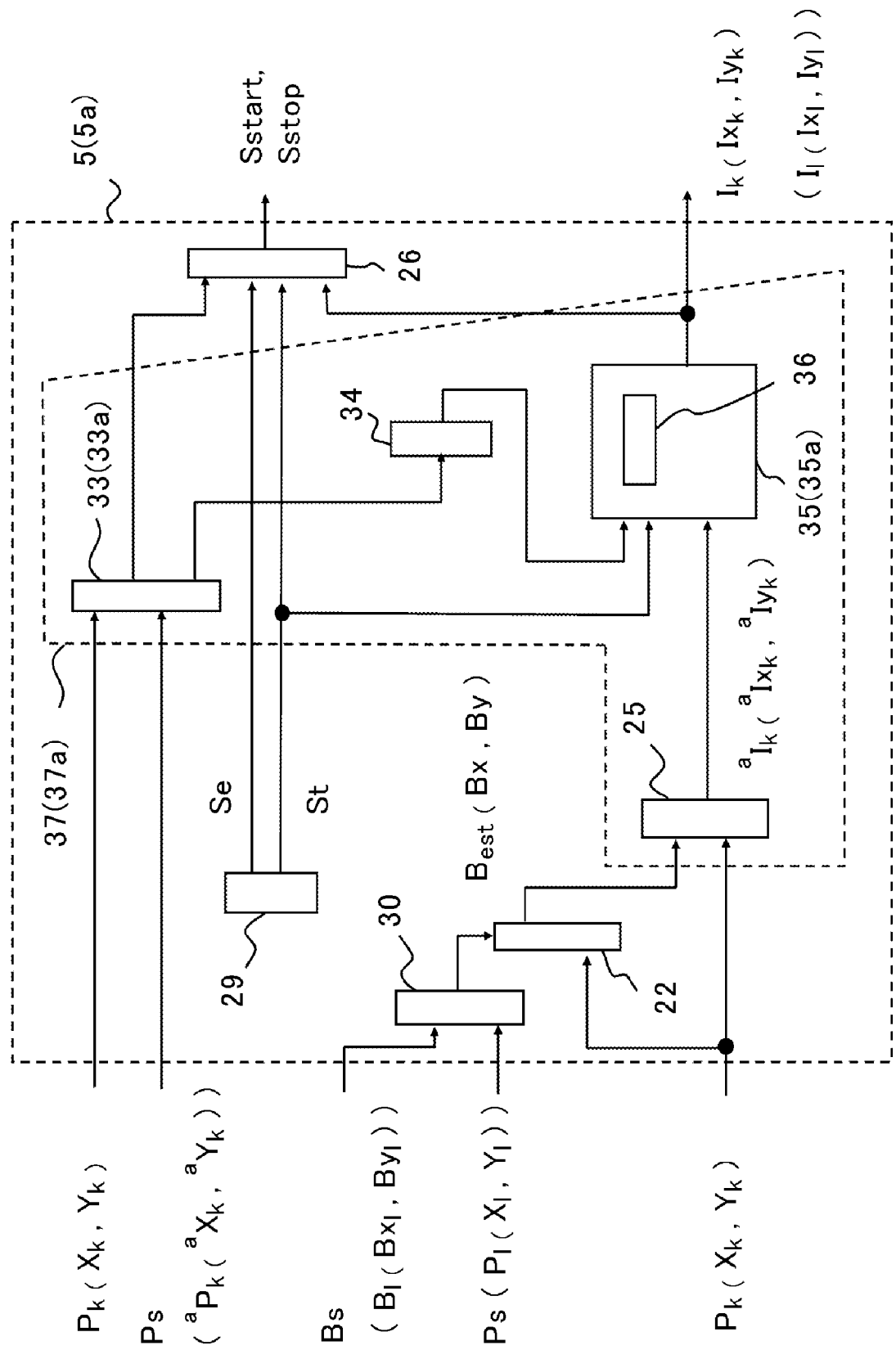
FIG. 2 is a block diagram of an irradiation control apparatus in FIG. 1.

FIG. 2 is a block diagram of the irradiation control apparatus 5. The irradiation control apparatus 5 is provided with an inverse map generator 30, an inverse map calculator 22, a command value outputting device 25, a command evaluator 33, a command updater 34, a scanning electromagnet command value series generator 35, and a beam supply command outputting device 26. The scanning electromagnet command value series generator 35 has a command value storage apparatus 36. The command value outputting device 25, the command evaluator 33, the command updater 34, the scanning electromagnet command value series generator 35 configure a scanning electromagnet command value learning generator 37. The scanning electromagnet command value learning generator 37 evaluates the result of a run-through, which is a series of irradiation operations through a command current $I_k$ ($Ix_k, Iy_k$) outputted from the scanning power source 4; when the result of the evaluation does not satisfy a predetermined condition, the command current $I_k$ ($Ix_k, Iy_k$) is updated and the run-through is implemented; then, the command current $I_k$ ($Ix_k$, $Iy_k$) such that its evaluation result has satisfied the predetermined condition is outputted to the scanning power source 4.

The operation of the irradiation control apparatus 5 will be explained. Irradiations by a particle beam therapy system are roughly divided into trial irradiation for calibration and actual irradiation for treatment. In general, because being irradiation for correction, trial irradiation for calibration is performed only when no patient exists and correction is required. Each time trial irradiation is performed while varying a control input (current Ix) to the X direction scanning electromagnet 3a and a control input (current Iy) to the Y direction scanning electromagnet 3b, the irradiation position is measured. In Embodiment 1, trial irradiation for calibration is performed in the same manner as in a conventional irradiation control apparatus; however, supply and stoppage of a charged particle beam is performed in a spot-scanning manner, and when the trial irradiation is performed, not only the measured irradiation position coordinates Ps (xs, ys) of a beam are measured, but also the measured magnetic field Bs (Bxs, Bys) is measured by use of the magnetic-field sensors 20a and 20b. By performing the trial irradiation in a spot-scanning manner, the measured irradiation position coordinates Ps (xs, ys) of a beam can accurately be measured. In this situation, the relationship between the measured magnetic field Bs (Bxs, Bys) of the scanning electromagnet 3 and the measured irradiation position coordinates Ps (xs, ys) of a beam is realized as a mathematical expression model, of the inverse map calculator 22, which is generated by the inverse map generator 30.

A command current $I_l$ ($Ix_l$, $Iy_l$) (the subscript "l" signifies a spot number in the trial irradiation) is preliminarily prepared for a trial irradiation (the step S001). The command current $I_l$ ($Ix_l$, $Iy_l$) for trial irradiation is prepared in such a way that a spot is irradiated within the assumed irradiation coverage of the particle beam irradiation apparatus 54. The command value outputting device 25 outputs the command current $I_l$ ($Ix_l$, $Iy_l$) to the scanning power source 4 (the step S002). The scanning power source 4 controls the scanning electromagnet 3 in accordance with the command current $I_l$ ($Ix_l$, $Iy_l$) (the step S003).

In synchronization with the command value outputting device 25, the beam supply command outputting device 26 waits for a sufficient stabilization time in which the magnetic fields of the scanning electromagnets 3a and 3b stabilize and then outputs a beam supply command $S_{start}$ for instructing the beam generation apparatus 51 to generate a beam. The beam generation apparatus 51 starts irradiation of a charged particle beam. After an irradiation time $T_{on}$ required for trial irradiation elapses, the beam supply command outputting device 26 outputs a beam stop command $S_{stop}$ for instructing the beam generation apparatus 51 to stop a beam, and then the beam generation apparatus 51 stops irradiation of a charged particle beam.

The magnetic-field sensors 20a and 20b measure the magnetic fields, of the scanning electromagnets 3a and 3b, that are controlled through the command current $I_l$ ($Ix_l$, $Iy_l$). A measured magnetic field $B_l$ ($Bx_l$, $By_l$) measured for each spot in trial irradiation is inputted to the inverse map generator 30 by way of the magnetic-field data converter 21.

The beam position monitor 7 calculates the irradiation position coordinates $P_l$ ($X_l$, $Y_l$) of an outgoing charged particle beam 1b with which scanning has been performed by the scanning electromagnet 3 for each spot. The irradiation position coordinates $P_l$ ($X_l$, $Y_l$) is inputted to the inverse map generator 30 by way of the position data converter 8.

The inverse map generator 30 stores in a memory the measured magnetic field $B_l$ ($Bx_l$, $By_l$) and the irradiation position coordinates $P_l$ ($X_l$, $Y_l$) of each spot, which is an incorporated storage device (the step S004).

The inverse map generator 30 creates a mathematical expression model, based on the stored measured magnetic field $B_l$ ($Bx_l$, $By_l$) and the stored measured irradiation position coordinates $P_l$ ($X_l$, $Y_l$), and stores the created mathematical expression model in the inverse map calculator 22 (the step S005).

The mathematical expression model for the inverse map calculator 22 is realized, as a preferred example, by use of a polynomial expression. There will be explained the reason why the inverse map calculator 22 is adopted instead of a conventional transformation table. Under the assumption that the specification of the scanning electromagnet 3, the specification of the scanning power source 4, and the specification of an irradiation beam (the irradiation energy, the incident beam position, and the like) are constant, if the magnetic field B (Bx, By) of the scanning electromagnet 3 is determined, the beam irradiation position coordinates P (x, y) is uniquely determined; thus, the physical phenomenon related to the relationship between the magnetic field B and the beam irradiation position coordinates P can be regarded as a positive map of two inputs and two outputs.

However, in the case of actual irradiation for treatment, the target irradiation position coordinates $P_{obj}$ ($Px_{obj}$, $Py_{obj}$) of a beam is preliminarily given, and it is required to control the magnetic field B (Bx, By) of the scanning electromagnet 3 so as to realize the target irradiation position coordinates $P_{obj}$ ($Px_{obj}$, $Py_{obj}$) of the beam. In other words, in the case of actual irradiation for treatment, it is required to calculate the estimated value $B_{est}$ ($\triangle Bx\triangledown$, $\triangle By\triangledown$) of the magnetic field B (Bx, By) of the scanning electromagnet 3, based on the target irradiation position coordinates $P_{obj}$ ($Px_{obj}$, $Py_{obj}$) of a beam, so as to realize the target irradiation position coordinates $P_{obj}$ ($Px_{obj}$, $Py_{obj}$) of the beam (with regard to the explanations for $\triangle Bx\triangledown$ and $\triangle By\triangledown$, refer to the mathematical expression (1) and the mathematical expression (2)). As described above, attention should be paid to the fact that, in actual irradiation, there is required an inverse map having a direction from the position to the magnetic field. Accordingly, in order to obtain the estimated value $B_{est}$ of the magnetic field B (Bx, By), the inverse map calculator 22 is required.

There will be explained the outline of the method of realizing the mathematical expression model for the inverse map calculator 22 by use of a polynomial expression. Here the polynomial expression signifies a polynomial commonly defined in mathematics; it is defined, for example, as "an expression consists only of constants, and the sums and the multiplication products of indeterminate elements". Specifically, it is exemplified by the following expression.

$$\hat{B}x = m_{00} + m_{01}Px_{obj} + m_{02}Px_{obj}^2 + m_{10}Py_{obj} + m_{11}Px_{obj}Py_{obj} + m_{20}Py_{obj}^2 \quad (1)$$

$$\hat{B}y = n_{00} + n_{01}Px_{obj} + n_{02}Px_{obj}^2 + n_{10}Py_{obj} + n_{11}Px_{obj}Py_{obj} + n_{20}Py_{obj}^2 \quad (2)$$

where $m_{00}, m_{01}, m_{02}, m_{10}, m_{11}, m_{20}, n_{00}, n_{01}, n_{02}, n_{10}, n_{11}, n_{20}$ are unknown parameter constants; and $Px_{obj}$, $Py_{obj}$ correspond to indeterminate elements in a polynomial expression. The left-hand side (Bx with a small "∩" on "B"; this is expressed by $\triangle Bx\triangledown$) of the equation (1) signifies an estimated value of Bx; the left-hand side (By with a small "∩" on "B"; this is expressed by $\triangle By\triangledown$) of the equation (2) signifies an estimated value of By. The estimated value $B_{est}$ of the magnetic field B (Bx, By) is expressed as ($\triangle Bx\triangledown$, $\triangle By\triangledown$).

The indeterminate parameter constants in a polynomial expression are obtained through the least square method or the like, based on the measured magnetic field $B_l$ ($Bx_l$, $By_l$) and the irradiation position coordinates $P_l$ ($X_l$, $Y_l$) for trial irradiation.

The estimated value $B_{est}$ of the magnetic field B (Bx, By) for realizing the target irradiation position coordinates $P_{obj}$ ($Px_{obj}$, $Py_{obj}$) is obtained from the equations (1) and (2) for which the obtained indeterminate parameter constants are substituted.

A conventional technology utilizes a method in which there is created, as a transformation table, the relationship between the control input (the command current $I_l$ ($Ix_l$, $Iy_l$)) to the scanning electromagnet 3 under calibration and the beam irradiation position coordinates $P_l$ ($X_l$, $Y_l$), and the transformation table is stored in the scanning electromagnet command value generator 6.

The control input (the command current $Ix_l$) to the X direction scanning electromagnet 3a and the control input (the command current $Iy_l$) to the Y direction scanning electromagnet 3b are independently obtained from the x coordinate value ($Px_{obj}$) of the beam target irradiation position coordinates $P_{obj}$ and from the y coordinate value ($Py_{obj}$) of the beam target irradiation position coordinates $P_{obj}$, respectively.

However, in practice, the control input (the command current $Ix_l$) to the X direction scanning electromagnet 3a affects both the x coordinate value and the y coordinate value of the beam target irradiation position coordinates P, and the control input (the command current $Iy_l$) to the Y direction scanning electromagnet 3b also affects both the x coordinate value and the y coordinate value of the beam target irradiation position coordinates P, i.e., there exists an interference term; therefore, the method utilizing a transformation table, which is independently obtained, deteriorates the accuracy of an irradiation position.

In the particle beam irradiation apparatus 54 according to Embodiment 1, in order to obtain the estimated value $B_{est}$ of the magnetic field B (Bx, By) for realizing the target irradiation position coordinates $P_{obj}$ ($Px_{obj}$, $Py_{obj}$), there is realized, in the inverse map calculator 22, a mathematical expression model where the interference terms are considered; therefore, unlike the conventional technology, the accuracy of the irradiation position of the outgoing charged particle beam 1b can be raised.

Next, there will be explained actual treatment irradiation in a particle beam therapy system according to Embodiment 1. Actual irradiation is divided into learning irradiation for optimizing the control of a beam irradiation position and a dose and therapy irradiation for irradiating a beam onto the irradiation subject 15 of a patient. The learning irradiation is performed in accordance with the following procedure.

For a certain irradiation subject 15, the treatment plan, among the treatment plans created by the treatment planning apparatus 55, which is finally selected by the doctor is converted into codes for driving the particle beam therapy system and transmitted to the irradiation control apparatus 5 (the step S101). In this description, it is assumed that the raster-scanning method is utilized in the learning irradiation and the therapy irradiation; the explanation will be made under the assumption that the codes for driving the particle beam therapy system is time-series data in which the irradiation orbit in each irradiation layer $Z_i$ (the subscript "i" signifies the layer number) is expressed by the irradiation position $P_k$ ($X_k$, $Y_k$) (the subscript "k" signifies the sequence number) in each sampling period.

A command current $I_k$ ($Ix_k$, $Iy_k$) (the subscript "k" signifies a sequence number) for learning irradiation is created through a method described later (the step S102). In the learning irradiation, a run-through is performed in accordance with the command current $I_k$ ($Ix_k$, $Iy_k$) for learning irradiation, under the condition that there exists no patient.

In an extreme case, anything may be utilized as the candidate of the command current $I_k$ ($Ix_k$, $Iy_k$) for learning irradiation or as the initial value for learning. In the present embodiment, what is obtained through the method according to a prior art is utilized as the initial value. The command current for learning irradiation is expressed as $^aI_k$ ($^aIx_k$, $^aIy_k$) (in this regard, "a" signifies the number of learning instances; in the case of the initial value, a=0); it is clearly described that the command current is updated each time learning is implemented.

The scanning electromagnet command value series generator 35 makes the command value storage apparatus 36 store the command current $^aI_k$ ($^aIx_k$, $^aIy_k$). The command current $^aI_k$ ($^aIx_k$, $^aIy_k$) is a control input in each sampling period; the subscript "k" signifies a sequence number. A run-through is performed in accordance with the initial-value command current $^0I_k$ ($^0Ix_k$, $^0Iy_k$) under the condition that there exists no patient (the step S103).

In response to a leaning irradiation start instruction by the operator of the particle beam therapy system, a actual irradiation start signal St, created by a signal generator 29, is transmitted to the beam supply command outputting device 26 and the scanning electromagnet command value series generator 35. The scanning electromagnet command value series generator 35 outputs the 0th-learning command current $^0I_k$ ($^0Ix_k$, $^0Iy_k$) in each sampling period, in accordance with the sequence number.

In response to the actual irradiation start signal St, the beam supply command outputting device 26 outputs to the beam generation apparatus 51 a beam supply command $S_{start}$ for generating a beam. The beam generation apparatus 51 starts irradiation of a charged particle beam.

The beam position monitor 7 detects the passing position of the outgoing charged particle beam 1b; $^aP_k$, which is the measured irradiation position coordinates Ps calculated by the position data converter 8, is inputted to the command evaluator 33. The command evaluator 33 compares the irradiation position $P_k$ ($X_k$, $Y_k$), which is the target irradiation position, with $^aP_k$ ($^aX_k$, $^aY_k$), which is the measured irradiation position coordinates Ps; then, the run-through with the initial-value command current $^0I_k$ ($^0Ix_k$, $^0Iy_k$) is scored (the step S104). The run-through scoring method will be described later.

The signal generator 29 transmits a actual irradiation end signal Se when actual irradiation is ended. The time when actual irradiation is ended means a time instant when a time corresponding to "sampling period×k (total sequence number)" has elapsed after actual irradiation is started. In response to the actual irradiation end signal Se, the beam supply command outputting device 26 outputs to the beam generation apparatus 51 the beam stop command $S_{stop}$ for stopping a beam. In response to the beam stop command $S_{stop}$, the beam generation apparatus 51 stops the charged particle beam 1a (the step S105).

Based on the result of scoring, which is the result of evaluation outputted from the command evaluator 33, the command updater 34 selects part of the sequence of 0th-learning command current $^aI_k$ ($^aIx_k$, $^aIy_k$), as the subject of alteration, and alters the sequence (the step S106). For example, the third sequence $^0I_3$ ($^0Ix_3$, $^0Iy_3$) of the 0th-learning command current $^0I_k$ ($^0Ix_k$, $^0Iy_k$) is altered from $^0Ix_3$ to ($^0Ix_3+\Delta I$).

Next, under the condition that there exists no patient, the run-through is implemented again by use of the command current, the sequence of which has partially been altered (the step S107). That is to say, the steps S103 through S105 are implemented as the second run-through.

It is assumed that partial alteration of the sequence has caused the result of scoring to change from J points to (J+ΔJ) points. Then, it can be understood that the third sequence $^0Ix_3$ of the command current may be updated by use of the information on ΔJ/ΔI. As is the case with a general learning function, in the case where, when ΔI is positive, the result of scoring is poor, there may be performed an update in which, for example, ΔI is changed to negative. This work may be implemented for every sequence that provides an effect on the result of scoring. This update causes the number of learning instances to be incremented by one ("a" is incremented to (a+1)).

The command updater 34 creates the updated 1st-learning command current $^aI_k$ ($^aIx_k$, $^aIy_k$) (the step S108). It is confirmed that the second run-through is superior to the first run-through in terms of the result of scoring; then, the learning is continued. The learning is repeated until a preliminarily set condition (such as a passing score) is satisfied. The command current $^aI_k$ ($^aIx_k$, $^aIy_k$) at a time when the learning has finally been completed is stored in the command value storage apparatus 36. In the case where, due to the learning, the result of scoring is deteriorated compared with the last run-through, the speed of update (the amount to be updated at one time) is lowered, or the command current is updated, as explained above.

The therapy irradiation is performed in accordance with the following procedure. In response to a therapy irradiation start instruction by the operator of the particle beam therapy system, the actual irradiation start signal St is transmitted to the beam supply command outputting device 26 and the scanning electromagnet command value series generator 35. The scanning electromagnet command value series generator 35 outputs the after-learning command current $^aI_k$ ($^aIx_k$, $^aIy_k$) in each sampling period, in accordance with the sequence number.

In response to the actual irradiation start signal St, the beam supply command outputting device 26 outputs to the beam generation apparatus 51 the beam supply command $S_{start}$ for generating a beam. The beam generation apparatus 51 starts irradiation of a charged particle beam (the step S109).

The signal generator 29 transmits the actual irradiation end signal Se when the actual irradiation is to be ended. The time when actual irradiation is ended means a time instant when a time corresponding to "sampling period×k (total sequence number)" has elapsed after actual irradiation is started. In response to the actual irradiation end signal Se, the beam supply command outputting device 26 outputs to the beam generation apparatus 51 the beam stop command $S_{stop}$ for stopping a beam. In response to the beam stop command $S_{stop}$, the beam generation apparatus 51 stops the charged particle beam 1a (the step S110).

Next, a run-through scoring method will be explained. In the most direct scoring method (a first scoring method), there is compared the time-series data in which the code for performing raster-scanning driving, i.e., the irradiation orbit for each irradiation layer $Z_i$ is expressed by the irradiation position $P_k$ ($X_k$, $Y_k$) (the subscript "k" signifies a sequence number) in each sampling period with the irradiation position $^aP_k$ ($^aX_k$, $^aY_k$) ("a" signifies the number of learning instances) in each sampling period at a time when a run-through has actually been performed, and then the following evaluation function is examined. When the value of the evaluation function becomes a predetermined value (when a predetermined condition is satisfied), the learning is ended.

$$J = \sum_k (({}^aX_k - X_k)^2 + ({}^aY_k - Y_k)^2) \quad (3)$$

The run-through scoring can also be performed through the following method (a second scoring method) while paying attention to an irradiation dose. In the run-through scoring, the target dose Di and the measured dose Ds are compared with each other in each of small regions defined, as represented in FIG. 4, in the magnetic field space, and the scoring is implemented in accordance with the score table T in FIG. 5. As far as the run-through evaluation is concerned, for example, the evaluation function is defined as the sum of the respective scores in the small regions defined in the magnetic field space, and based on the score of the evaluation function, the evaluation is implemented. It is determined that the run-through with a higher score of the evaluation function is superior to the run-through with a lower score. FIG. 4 is a table representing a magnetic-field small region $S_{i,j}$ defined by the magnetic-field space (Bx, By); FIG. 5 represents an example of score table T at a time when learning irradiation is performed. In addition, the target dose Di for a small region is calculated by the treatment planning apparatus. The measured dose Ds is obtained from the result of measurement by the beam position monitor 7, the time instant when the charged particle beam 1b passes through the small region, and the like.

Figure 3:
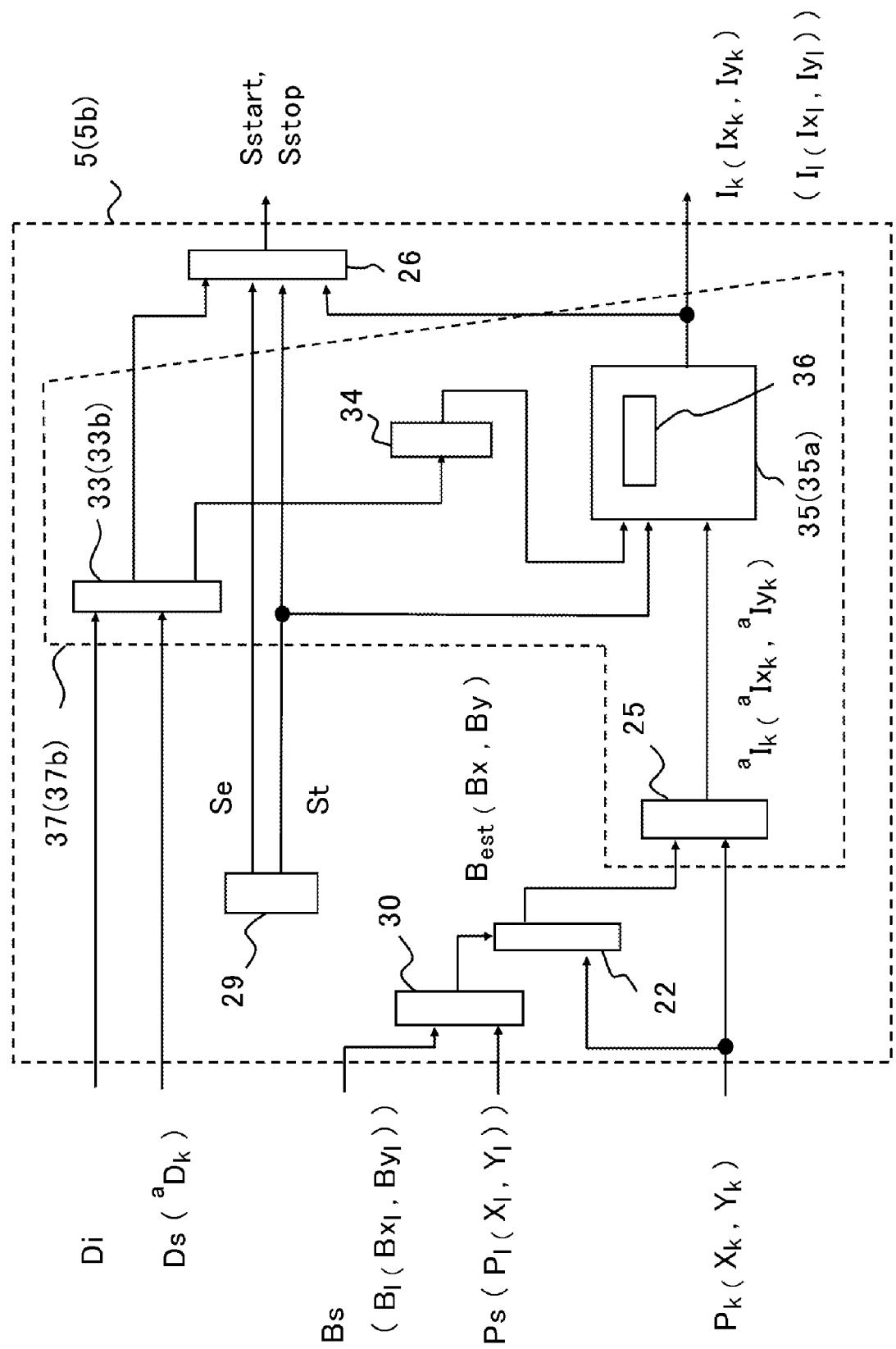
FIG. 3 is a block diagram of another irradiation control apparatus in FIG. 1.

In the second run-through scoring method, as illustrated in FIG. 3, the signal inputted to the command evaluator 33 is different. Because of this, the step S104 is different. FIG. 3 is a block diagram of an irradiation control apparatus in which the second run-through scoring method is adopted. The target dose Di and the measured dose Ds ($^aD_k$) are inputted to a command evaluator 33b of a scanning electromagnet command value learning generator 37b in an irradiation control apparatus 5b. In the step S104, the dose monitor 11 detects the dose, and the measured dose Ds obtained through conversion by the dose data converter 12 is inputted to the command evaluator 33b. The command evaluator 33b compares the target dose Di with the measured dose Ds, and then scores the run-through with the initial-value command current $^0I_k$ ($^0Ix_k$, $^0Iy_k$).

In FIG. 4, ($B_0$, $B_1$) in the left column of the table briefly represents that the X component Bx of the magnetic field B satisfies the relationship $B_0 \leq Bx < B_1$; similarly, ($B_{m-1}$, $B_m$) briefly represents that Bx satisfies the relationship $B_{m-1} \leq Bx < B_m$. ($B_0$, $B_1$) in the top row of the table briefly represents that the Y component By of the magnetic field B satisfies the relationship $B_0 \leq By < B_1$; similarly, ($B_{m-1}$, $B_m$) briefly represents that By satisfies the relationship $B_{m-1} \leq By < B_m$. The region $S_{0,0}$ is a region in which the relationships $B_0 \leq Bx < B_1$ and $B_0 \leq By < B_1$ are satisfied; the region $S_{m-1,m-1}$ is a region in which the relationships $B_{m-1} \leq Bx < B_m$ and $B_{m-1} \leq By < B_m$ are satisfied.

The scoring of the run-through is performed in the whole region of the magnetic-field space corresponding to the irradiation coverage of the particle beam irradiation apparatus 54. Accordingly, the irradiation subject 15 of a patient is administered through the target dose Di, and the site, other than the irradiation subject 15, corresponding to a normal tissue is administered in such a way that the dose therefor is "zero"; therefore, the dose of a charged particle beam in the irradiation subject 15 and non-irradiation subject can accurately be administered.

Once the magnetic field of the scanning electromagnet 3 is determined, the irradiation position of a charged particle beam is uniquely determined. In other words, the magnetic field of the scanning electromagnet 3 is in a one-to-one relationship with the irradiation position of a charged particle beam. Therefore, unlike the region defined in the command current space in a prior art, the hysteresis of the scanning electromagnet does not provide any effect on the irradiation of a charged particle beam. In addition, the relationship, between the magnetic field detected by the magnetic-field sensor 20 and the beam position detected by the beam position monitor 7, which is obtained by performing calibration irradiation of a charged particle beam coincides very well with the relationship between the magnetic field and the beam position in the case of actual irradiation where irradiation of a charged particle beam is performed in the same manner as the calibration irradiation. An actual irradiation space can be obtained through the outgoing position of a charged particle beam, the passing position in the beam position monitor 7, and the positional relationship between the particle beam irradiation apparatus 54 and the irradiation subject 15; thus, a region in the actual irradiation space has a mapping relationship with a region defined in the magnetic-field space, and this mapping relationship hardly changes even in the case of actual irradiation. Accordingly, because the scoring of the run-through is performed for each of small magnetic field regions $S_{i,j}$ defined in the magnetic-field space, and charged particle beam dose administration is performed for each of the small magnetic field regions $S_{i,j}$, the dose administration for the irradiation subject 15 in the actual irradiation space can accurately be performed.

The score table T, represented in FIG. 5, at a time when learning irradiation is performed is an example of scoring by deducting points. A dose error de is a difference obtained by subtracting the target dose Di from a measured regional dose Dss. The measured regional dose Dss is an actual irradiation amount in the small magnetic field region $S_{i,j}$ defined in the magnetic-field space (Bx, By) and is created from the measured magnetic field Bs measured by the magnetic-field sensor 20 and the measured dose Ds measured by the dose monitor 11. Δd is the range of the dose error and is set to a predetermined value, which is within a tolerance range. The absolute value of the score changing rate in the case where the measured dose Ds exceeds the target dose Di is set to be larger than the absolute value of the score changing rate in the case where the measured dose Ds is smaller than the target dose Di. As a result, in the case where the measured dose Ds exceeds the target dose Di, correction can rapidly and accurately be implemented.

In the particle beam irradiation apparatus 54, utilizing the first scoring method, according to Embodiment 1, an actual irradiation position is utilized as the evaluation function; thus, the command current $^aI_k$ ($^aIx_k$, $^aIy_k$) to the scanning electromagnet 3 can suitably be learned. In the particle beam irradiation apparatus 54, utilizing the second scoring method, according to Embodiment 1, scoring is performed based on the target dose Di and the measured regional dose Dss, for each of the magnetic field small regions $S_{i,j}$ defined in the magnetic-field space (Bx, By), and based on the scores, the evaluation function is defined; therefore, the command current $^aI_k$ ($^aIx_k$, $^aIy_k$) to the scanning electromagnet 3 can suitably be learned. Accordingly, a high-accuracy high-safety particle beam irradiation apparatus can be provided.

In the particle beam irradiation apparatus 54, in the first scoring method, there is utilized, as the evaluation function, the actual irradiation position in which the effect of the hysteresis produced between the current and the magnetic field of the scanning electromagnet 3 is reflected, so the command current $^aI_k$ ($^aIx_k$, $^aIy_k$) to the scanning electromagnet 3 is suitably be learned; thus, the hysteresis produced between the current and the magnetic field of the scanning electromagnet 3 can be eliminated. Through the second scoring method, the particle beam irradiation apparatus 54 performs dose administration for a charged particle beam for each of magnetic-field small regions $S_{i,j}$ defined in the magnetic-field space (Bx, By); thus, the hysteresis produced between the current and the magnetic field of the scanning electromagnet 3 can be eliminated. As a result, the effect of the hysteresis of the scanning electromagnet is eliminated, so that high-accuracy beam irradiation can be realized.

The magnetic-field sensor 20 may be a magnetic-field sensor having a hall device. Because utilizing a hall device makes it possible to measure the absolute value of the magnetic field generated by the scanning electromagnet 3, it is not required to perform calculation, such as integration, of a voltage measured by a pickup coil. As a result, the magnetic-field data converter 21 can be simplified and downsized.

A magnetic-field sensor having both a pickup coil and a hall device is most desirable, as the magnetic-field sensor 20. That is because there can be obtained both the hall device's advantage in which the absolute value of the magnetic field can be measured and the pickup coil's advantage in which the variation of the magnetic field can be measured without any effect of the hysteresis.

In a conventional particle beam irradiation apparatus, a beam irradiation position has been detected only with a single beam position monitor or a plurality of beam position monitors, and a charged particle beam has been feedback-controlled based on measured irradiation position coordinates. Arranging a great number of devices, such as a position monitor and the like, that cut off a charged particle beam leads to the enlargement of beam dispersion; thus, there has been a problem that a desired beam spot diameter cannot be obtained.

In the particle beam irradiation apparatus 54 according to Embodiment 1, while therapy irradiation is performed, the scanning electromagnet command value series generator 35 outputs, in each sampling period, the after-learning command current $^aI_k$ ($^aIx_k$, $^aIy_k$) in accordance with the sequence number so as to perform control of the irradiation position of a charged particle beam and the irradiation dose; therefore, the particle beam irradiation system 54 may be configured in such a way that in the case of actual irradiation, the beam position monitor 7 is moved by an unillustrated moving apparatus so that the outgoing charged particle beam 1b does not pass through the beam position monitor 7. The foregoing method can prevent the outgoing charged particle beam 1b from being dispersed and enlarged by the beam position monitor 7. Accordingly, the beam spot diameter can be reduced. As a result, in the case where it is better to perform irradiation with a beam having a small diameter, treatment can be carried out with a suitable spot diameter.

It may also be allowed that the command value outputting device 25 creates the command current $I_k$ ($Ix_k$, $Iy_k$) based on the estimated value $B_{est}$ of the magnetic field B (Bx, By) of the scanning electromagnet 3 and by means of the run-through implemented utilizing the command current $I_k$ as the initial value, learning can be performed.

In addition, the explanation has been made with an example where the irradiation control apparatus 5 has the inverse map generator 30 and the inverse map calculator 22; however, it goes without saying that, even in the case where the irradiation control apparatus 5 has neither the inverse map generator 30 nor the inverse map calculator 22, it is made possible to eliminate the effect of the hysteresis of the scanning electromagnet and to realize high-accuracy beam irradiation in the raster-scanning and the hybrid scanning.

As described above, the particle beam irradiation apparatus 54 according to Embodiment 1 is provided with the scanning power source 4 that outputs the excitation current for the scanning electromagnet 3 and the irradiation control apparatus 5 that controls the scanning power source 4. The irradiation control apparatus 5 is provided with the scanning electromagnet command value learning generator 37 that evaluates the result of a run-through, which is a series of irradiation operations through the command value $I_k$ for the excitation current outputted from the scanning power source 4, that updates the command value $I_k$ for the excitation current, when the result of the evaluation does not satisfy a predetermined condition, so as to perform the run-through, and that outputs to the scanning power source 4 the command value $I_k$ for the excitation current such that its evaluation result has satisfied the predetermined condition. Therefore, based on the result of the run-through, the scanning electromagnet command value learning generator 37 can suitably learn the excitation-current command value $I_k$ outputted to the scanning power source 4; thus, the effect of the hysteresis of the scanning electromagnet is eliminated, so that high-accuracy beam irradiation can be realized in the raster-scanning and the hybrid scanning.

In a particle beam therapy system according to Embodiment 1, there are provided the beam generation apparatus 51 that generates a charged particle beam, the accelerator 52 that accelerates a charged particle beam generated by the beam generation apparatus 51, the beam transport apparatus 53 that transports a charged particle beam accelerated by the accelerator 52, and the particle beam irradiation system 54 that, by the scanning electromagnet 3, performs scanning with a charged particle beam transported by the beam transport apparatus 53 and emits the charged particle beam onto the irradiation subject 15; the particle beam irradiation apparatus 54 is provided with the scanning power source 4 that outputs the excitation current for the scanning electromagnet 3 and the irradiation control apparatus 5 that controls the scanning power source 4. The irradiation control apparatus 5 is provided with the scanning electromagnet command value learning generator 37 that evaluates the result of a run-through, which is a series of irradiation operations through the command value $I_k$ for the excitation current outputted from the scanning power source 4, that updates the command value $I_k$ for the excitation current, when the result of the evaluation does not satisfy a predetermined condition, so as to perform the run-through, and that outputs to the scanning power source 4 the command value $I_k$ for the excitation current such that its evaluation result has satisfied the predetermined condition. Therefore, based on the result of the run-through, the scanning electromagnet command value learning generator 37 can suitably learn the excitation-current command value $I_k$ outputted to the scanning power source 4; thus, as a result, the effect of the hysteresis of a scanning electromagnet is eliminated, so that high-accuracy particle beam therapy can be realized by utilizing high-accuracy beam irradiation in the raster-scanning or in the hybrid scanning.

Embodiment 2

In Embodiment 1, in the learning irradiation for the actual irradiation, a charged particle beam is irradiated; however, it is made possible to learn without irradiating a charged particle beam and optimize the command current $I_k$ ($Ix_k$, $Iy_k$). The method therefor will be explained. In a particle beam therapy system according to Embodiment 2, as the scoring method for the run-through of learning irradiation, two kinds of run-through scoring methods (a third scoring method and a fourth scoring method) can be utilized. In the third scoring method, there is compared the time-series data in which the code for performing raster-scanning driving, i.e., the irradiation orbit for each irradiation layer $Z_i$ is expressed by $B_k$ ($Bx_k$, $By_k$), which is the estimated value $B_{est}$ of the magnetic field corresponding to the irradiation position $P_k$ ($X_k$, $Y_k$) (the subscript "k" signifies a sequence number) in each sampling period, with the measured magnetic field $^aB_k$ ($^aBx_k$, $^aBy_k$) ("a" signifies the number of learning instances) in each sampling period at a time when a run-through has actually been performed, and then the following evaluation function is examined. The estimated value $B_k$ of the magnetic field is calculated by the inverse map calculator 22.

$$J = \sum_k (({}^aBx_k - Bx_k)^2 + ({}^aBy_k - By_k)^2) \tag{4}$$

In the fourth scoring method, scoring is implemented in accordance with the score table T in FIG. 5 However, irradiation of a charged particle beam is not implemented when learning irradiation is performed; therefore, unlike Embodiment 1, the dose error de is a difference obtained by subtracting the target dose Di from the calculated regional dose value Dsc. The calculated regional dose value Dsc is obtained by integrating the dose for a time during which the outgoing charged particle beam 1b stays in each of magnetic-field small region $S_{i,j}$ defined in the magnetic-field space (Bx, By) based on the measured magnetic field $^aB_k$ ($^aBx_k$, $^aBy_k$) measured by the magnetic-field sensor 20.

Figure 6:
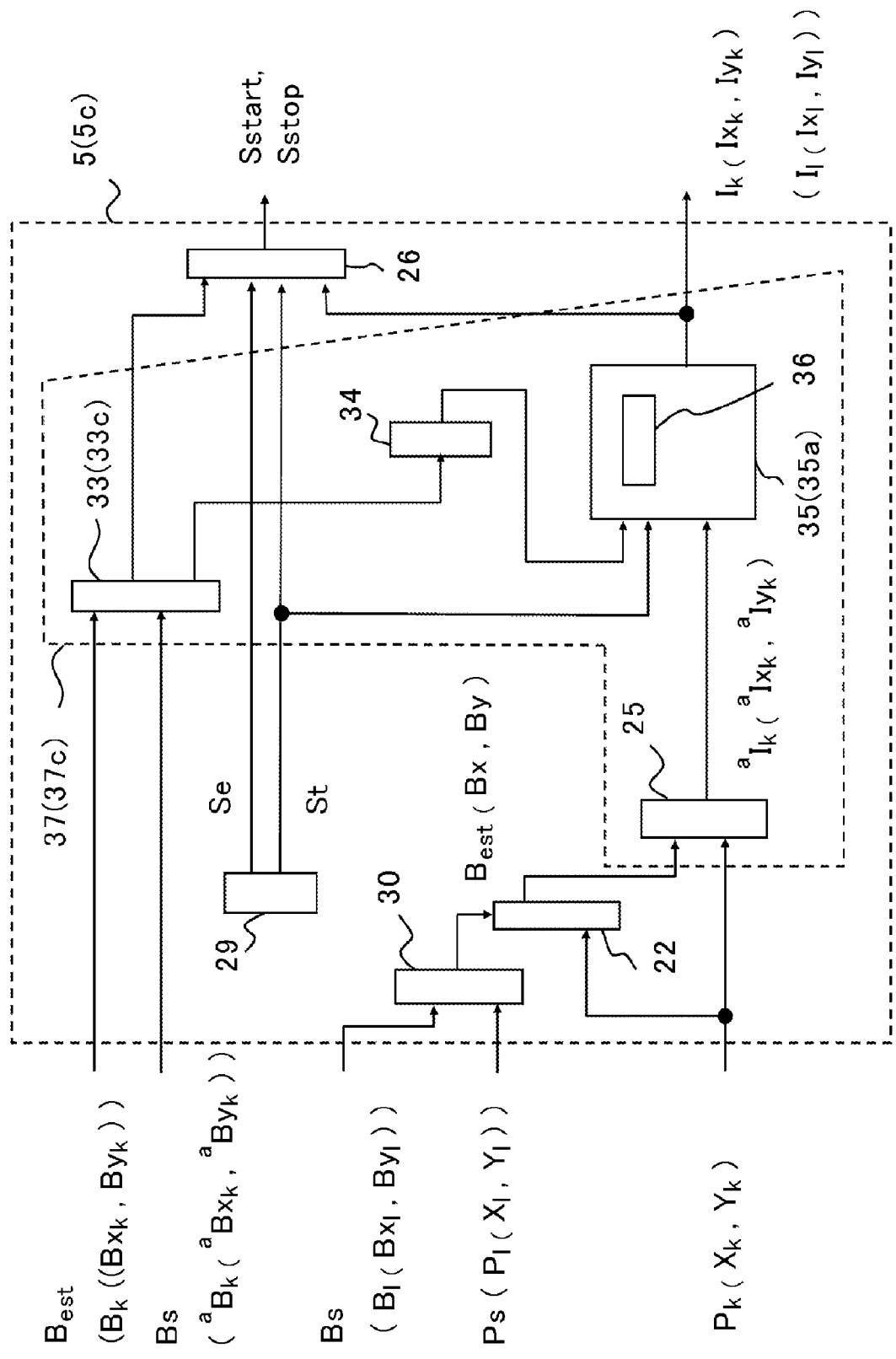
FIG. 6 is a block diagram of an irradiation control apparatus according to Embodiment 2 of the present invention.

FIG. 6 is a block diagram of an irradiation control apparatus according to Embodiment 2 of the present invention; as the scoring method for the run-through of learning irradiation, the third scoring method is adopted. The irradiation control apparatus according to Embodiment 2 is different from the irradiation control apparatus according to Embodiment 1 in terms of signals inputted to the command evaluator 33. The estimated value $B_k$ ($Bx_k$, $By_k$) of the magnetic field and the measured magnetic field $^aB_k$ ($^aBx_k$, $^aBy_k$) are inputted to a command evaluator 33c of a scanning electromagnet command value learning generator 37c in an irradiation control apparatus 5c. The operation of the irradiation control apparatus 5c according to Embodiment 2 will be explained. The trial irradiation at a time when calibration is performed is similar to the trial irradiation implemented in accordance with the steps S001 through S005 in Embodiment 1. Although the learning irradiation is basically the same as that implemented in accordance with the steps S101 through S108 in Embodiment 1, the irradiation of a charged particle beam is not performed; thus, the step S104 is different. Instead of the step S104 in Embodiment 1, the step S201 is implemented.

The magnetic-field sensors 20a and 20b measure the magnetic fields produced by the scanning electromagnets 3a and 3b that are controlled through the command current $I_k$ ($Ix_k$, $Iy_k$). The measured magnetic field $^aB_k$ ($^aBx_k$, $^aBy_k$), measured by the magnetic-field sensor 20 and converted by the magnetic-field data converter 21, is inputted to the command evaluator 33c. The command evaluator 33c compares the estimated value $B_k$ ($Bx_k$, $By_k$) of the magnetic field, which is calculated by the inverse map calculator 22 for each sequence number, with the measured magnetic field $^aB_k$ ($^aBx_k$, $^aBy_k$); then, the run-through with the initial-value command current $^0I_k$ ($^0Ix_k$, $^0Iy_k$) is scored (the step S201).

Figure 7:
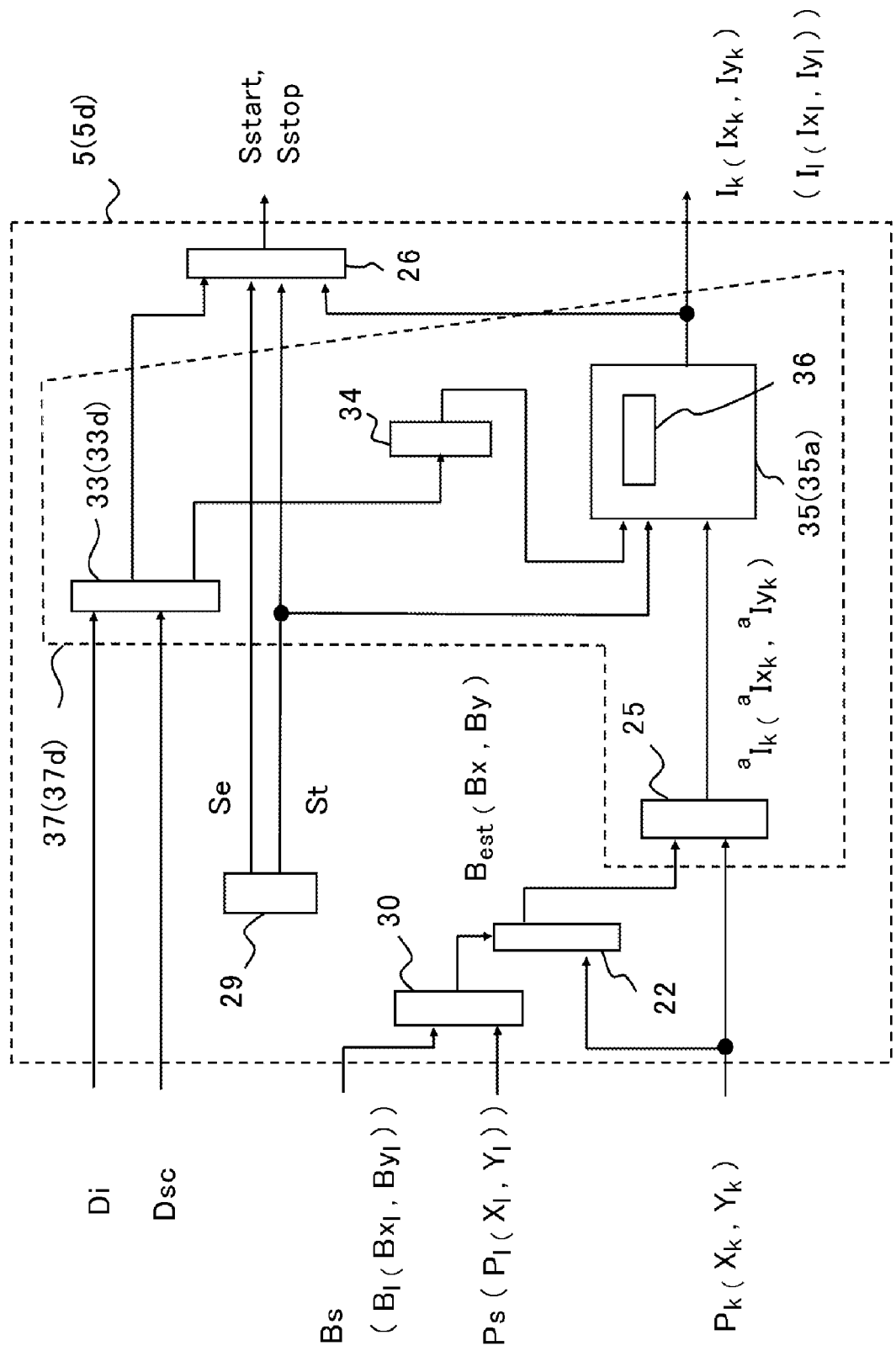
FIG. 7 is a block diagram of another irradiation control apparatus according to Embodiment 2 of the present invention.

Next, there will be explained an irradiation control apparatus and the operation thereof, in the case where, as the scoring method for the run-through of learning irradiation, the fourth scoring method is adopted. FIG. 7 is a block diagram of another irradiation control apparatus according to Embodiment 2 of the present invention; as the scoring method for the run-through of learning irradiation, the fourth scoring method is adopted. The foregoing irradiation control apparatus according to Embodiment 2 is different from the irradiation control apparatus according to Embodiment 1 in terms of signals inputted to the command evaluator 33. The target dose Di and the calculated regional dose value Dsc are inputted to a command evaluator 33d of a scanning electromagnet command value learning generator 37d in an irradiation control apparatus 5d. The operation of the irradiation control apparatus 5d according to Embodiment 2 will be explained. The trial irradiation at a time when calibration is performed is similar to the trial irradiation implemented in accordance with the steps S001 through S005 in Embodiment 1. Although the learning irradiation is basically the same as that implemented in accordance with the steps S101 through S108 in Embodiment 1, the irradiation of a charged particle beam is not performed; thus, the step S104 is different. Instead of the step S104 in Embodiment 1, the step S202 is implemented.

The calculated regional dose value Dsc is obtained by integrating the dose for a time during which the charged particle beam 1 controlled through the command current $I_k$ ($Ix_k$, $Iy_k$) stays in each of magnetic-field small region $S_{i,j}$, and is inputted to the command evaluator 33d. The command evaluator 33c compares the target dose Di with the calculated regional dose value Dsc and then scores the run-through with the initial-value command current $^0I_k$ ($^0Ix_k$, $^0Iy_k$) (the step S202).

In the particle beam irradiation apparatus 54, utilizing the third scoring method, according to Embodiment 2, a measured magnetic field is utilized as the evaluation function; thus, the command current $^aI_k$ ($^aIx_k$, $^aIy_k$) to the scanning electromagnet 3 can suitably be learned. In the particle beam irradiation apparatus 54, utilizing the fourth scoring method, according to Embodiment 2, scoring is performed based on the target dose Di and the calculated regional dose value Dsc calculated for each of the magnetic-field small regions $S_{i,j}$ defined in the magnetic-field space (Bx, By), and based on the scores, the evaluation function is defined; therefore, the command current $^aI_k$ ($^aIx_k$, $^aIy_k$) to the scanning electromagnet 3 can suitably be learned without irradiating a charged particle beam. Accordingly, a high-accuracy high-safety particle beam irradiation apparatus can be provided.

In the particle beam irradiation apparatus 54, in the third scoring method, there is utilized, as the evaluation function, the measured magnetic field so that the command current $^aI_k$ ($^aIx_k$, $^aIy_k$) to the scanning electromagnet 3 is suitably learned; therefore, the effect of the hysteresis produced between the current and the magnetic field of the scanning electromagnet 3 can be eliminated. Through the fourth scoring method, the particle beam irradiation apparatus 54 performs dose administration for a charged particle beam for each of magnetic-field small regions $S_{i,j}$ defined in the magnetic-field space (Bx, By); thus, the hysteresis produced between the current and the magnetic field of the scanning electromagnet 3 can be eliminated. As a result, the effect of the hysteresis of the scanning electromagnet is eliminated, so that high-accuracy beam irradiation can be realized.

Because the run-through of the learning irradiation can be implemented without irradiating a charged particle beam, wasteful energy consumption can be suppressed.

Embodiment 3

The learning function can be interpreted as a "function of approaching the solution that is as ideal for a problem as possible". In Embodiments 1 and 2, there has been explained a function of creating the command current $I_k$ ($Ix_k$, $Iy_k$) for realizing irradiation that is as ideal as possible for the problem as to how the actual irradiation can be made close to the treatment plan data created for each patient by the treatment planning apparatus 55.

In the control engineering, a more advanced learning function (or a more intelligent learning function) is interpreted as a "function capable of obtaining, based on the accumulated past experiences, a solution that is as ideal as possible for a future and unknown problem". Thus, in Embodiment 3, there will be explained a particle beam irradiation apparatus and a particle beam therapy system in which the learning function explained in Embodiment 1 or 2 is further applied, and a more advanced learning function is provided.

In the learning irradiation according to Embodiment 1, run-through is scored, and based on the result of the scoring, the command current $I_k$ is updated to a more suitable one. According to this method, there can be created the command current $I_k$ for realizing irradiation that is as ideal as possible for treatment plan data; however, the experience here cannot be reflected in other treatment plan data items.

In the learning irradiation according to Embodiment 3, scoring of run-through is performed as is the case with Embodiment 1 or 2. However, the command current $I_k$ ($Ix_k$, $Iy_k$) is not updated based on the result of scoring of the run-through; a mathematical model for creating the command current $I_k$ ($Ix_k$, $Iy_k$) is provided, and the parameter of the mathematical model is updated to the optimal one. The detail thereof is explained below.

Figure 8:
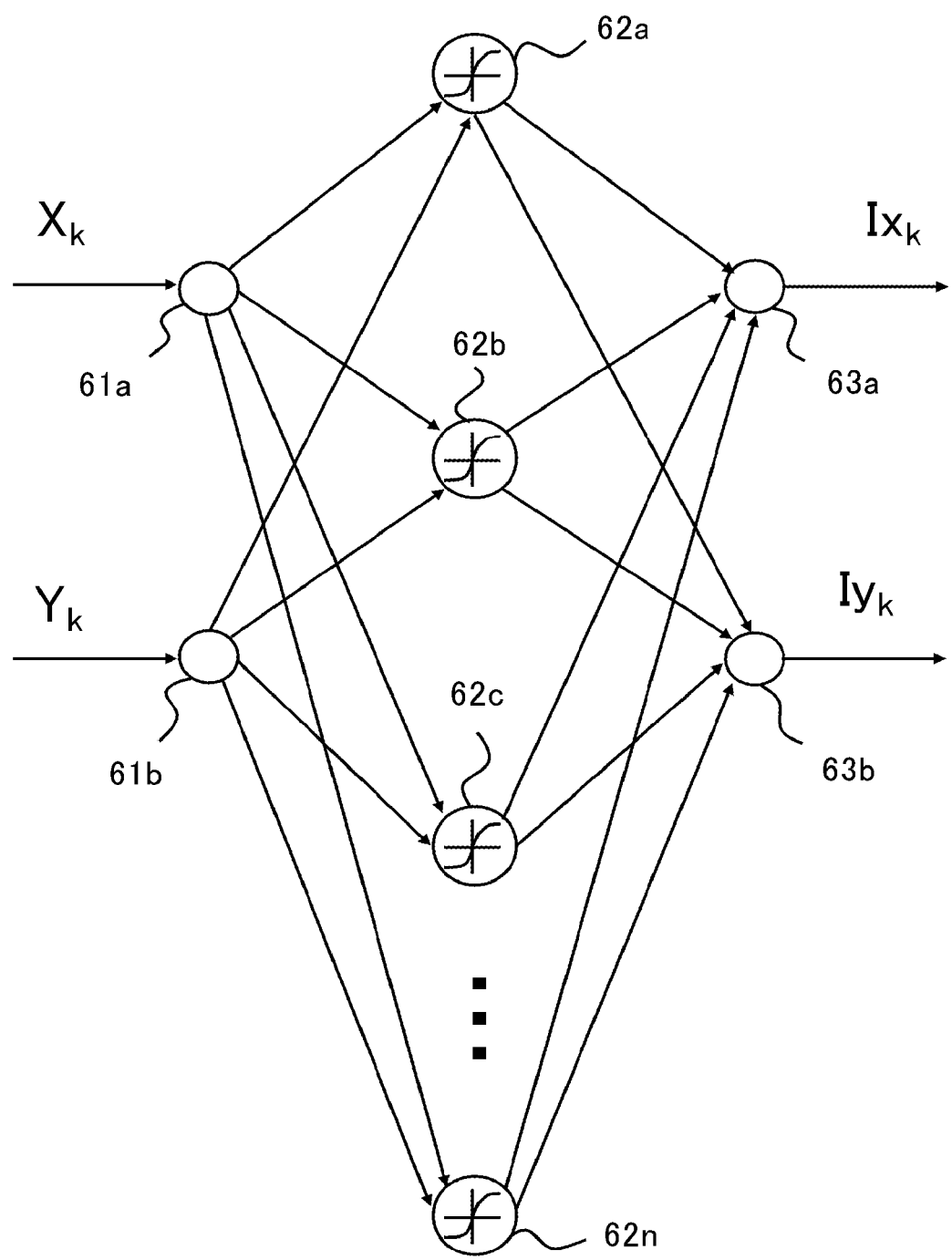
FIG. 8 is an example of mathematical model for generating a command current in Embodiment 3 of the present invention.

FIG. 8 is a chart representing an example of mathematical model for creating the command current $I_k$ ($Ix_k$, $Iy_k$) in Embodiment 3. There will be explained the method of creating the command current $I_k$ ($Ix_k$, $Iy_k$) based on FIG. 8.

A feed-forward type NN (neural network; referred to as "NN", hereinafter) 60 having hidden layers (each of them is single-layer) is an example of mathematical model for creating the command current $I_k$ ($Ix_k$, $Iy_k$). An input layer 61 is the input unit of NN 60; in Embodiment 3 of the present invention, the target irradiation position $P_k$ ($X_k$, $Y_k$) in each sampling period corresponds to the input layer 61. $X_k$ is inputted to an input layer 61a, and $Y_k$ is inputted to an input layer 61b. An output layer 63 is the output unit of NN 60; in Embodiment 3 of the present invention, the command current $I_k$ ($Ix_k$, $Iy_k$) corresponds to the output layer 63. $Ix_k$ is outputted to an output layer 63a, and $Iy_k$ is outputted to an output layer 63b. A hidden layer 62 is the basis function (activation function) of NN 60; the input signals from the input layers 61a and 61b are weighted by a plurality of hidden layers 62a through 62n and outputted to the output layers 63a and 63b.

In a particle beam therapy system, the scanning electromagnet 3 deflects the charged particle beam 1, so that the irradiation position thereof is determined. That is to say, once a series of command currents $I_k$ ($Ix_k$, $Iy_k$) to the scanning electromagnet 3 is determined, the irradiation position coordinates P (X, Y) of a beam is uniquely determined; therefore, the physical phenomenon ranging from the series of command currents $I_k$ ($Ix_k$, $Iy_k$) to the irradiation position coordinates P (X, Y) of a beam can be regarded as a 2-input 2-output system having dynamics of hysteresis characteristics. What is to be mathematically realized by NN 60 is the 2-input 2-output inverse system having dynamics of hysteresis characteristics.

In Embodiments 1 and 2, the command current $I_k$ ($Ix_k$, $Iy_k$) itself is updated in learning irradiation. In contrast, in Embodiment 3, the weighting by the hidden layer 62 of NN 60 is updated. In FIG. 9, there is illustrated an irradiation control apparatus 5 (5e) provided with a scanning electromagnet command value series generator 35b having NN 60. The irradiation control apparatus 5e is an example of an irradiation control apparatus in which the inverse map generator 30, the inverse map calculator 22, the command value outputting device 25, and the command updater 34 are removed from the irradiation control apparatus 5a of Embodiment 1, a scanning electromagnet command value learning generator 37e has a parameter updater 38, and the scanning electromagnet command value series generator 35 is provided with NN 60. In the irradiation control apparatus 5e, the first scoring method is utilized as the scoring method for the run-through of learning irradiation. The parameter updater 38 updates the weighting by the hidden layer 62, which is the parameter of NN 60, in such a way that the result of scoring by the command evaluator 33 satisfies a predetermined condition. In the irradiation control apparatus 5 provided with the scanning electromagnet command value series generator 35b having NN 60, each of the second method, the third method and the fourth method may be utilized as the scoring method for the run-through of learning irradiation. In this case, the command evaluator 33a in FIG. 9 may be replaced by each command evaluator which is any one of the command evaluator 33b to 33d. In addition, in the case of the third scoring method, the irradiation control apparatus 5 may be provided with the inverse map generator 30 and the inverse map calculator 22, and the magnetic-field estimated value $B_k$ may be obtained through calculation by the inverse map calculator 22.

By configuring as described above, in the particle beam therapy system according to Embodiment 3 of the present invention, the experience in learning irradiation run-through (learning run-through) for treatment plan data is accumulated. In the case where a great deal of experience in the learning run-through has been accumulated, it is not required to implement learning run-through for each new treatment plan data; therefore, there can efficiently be obtained a particle beam therapy system that is not liable to undergo the effect of the hysteresis of the scanning electromagnet and performs high-accuracy irradiation.

In addition, the algorithm explained in each of Embodiments 1 to 3 is only an example; another algorithm, such as the steepest descent method or the genetic algorithm, which is utilized in other technical fields may be adopted.

Moreover, the evaluation function in performing evaluation of run-through is not limited to the functions explained herein; other evaluation functions may be utilized. Weighting may be implemented for each sequence number k in the equation (3) or (4). Still moreover, in performing scoring for each of a plurality of small regions defined in the magnetic-field space, there may be utilized an evaluation function obtained by adding the scores $Sc_{i,j}$ to which weighting $w_{i,j}$ are applied, in the respective small regions. In these cases, the important position and region can accurately be optimized.

INDUSTRIAL APPLICABILITY

A particle beam irradiation apparatus and a particle beam therapy system according to the present invention can suitably be applied to a particle beam therapy system utilized in the medical field and R&Ds.

DESCRIPTION OF REFERENCE NUMERALS

1: charged particle beam
1a: incident charged particle beam
1b: outgoing charged particle beam
3: scanning electromagnet
3a: X direction scanning electromagnet
3b: Y direction scanning electromagnet
4: scanning power source
7: beam position monitor
11: dose monitor
15: irradiation subject
20: magnetic-field sensor
20a: magnetic-field sensor for X direction scanning electromagnet
20b: magnetic-field sensor for Y direction scanning electromagnet
22: inverse map calculator
33: command evaluator
34: command updater
35: scanning electromagnet command value series generator
35a: scanning electromagnet command value series generator
35b: scanning electromagnet command value series generator
37: scanning electromagnet command value learning generator
37a: scanning electromagnet command value learning generator
37b: scanning electromagnet command value learning generator
37c: scanning electromagnet command value learning generator
37d: scanning electromagnet command value learning generator
37e: scanning electromagnet command value learning generator
38: parameter updater
51: beam generation apparatus
52: accelerator
53: beam transport apparatus
54: particle beam irradiation apparatus
60: NN (neural network)
Ps: measured irradiation position coordinates
$^aP_k$: irradiation position
$P_k$: irradiation position
Ds: measured dose
$^aD_k$: measured dose
Di: target dose
Bs: measured magnetic field
$^aB_k$: measured magnetic field
$B_{est}$: magnetic-field estimated value
$B_k$: magnetic-field estimated value
Dss: measured regional dose
Dsc: calculated regional dose value
de: dose error
T: score table
$S_{i,j}$: magnetic-field small region
$I_k$: command current

The invention claimed is:

1. A particle beam irradiation apparatus comprising:
a scanning electromagnet that scans a charged particle beam accelerated by an accelerator and has a hysteresis;
a scanning power source that outputs an excitation current for driving the scanning electromagnet; and
an irradiation control apparatus that controls the scanning power source, wherein the irradiation control apparatus has a scanning electromagnet command value learning generator that (i) has a mathematical model for generating a command value for the excitation current, (ii) evaluates the result of a run-through, which is a series of irradiation operations through a command value for the excitation current outputted from the scanning power source, and (iii) updates the mathematical model, based on the result of the evaluation, (iv) accumulates experiences in the run-through, and (v) outputs to the scanning power source the command value for the excitation current to be generated, based on the accumulated experiences of the run-through, by the mathematical model.

2. The particle beam irradiation apparatus according to claim 1, wherein the scanning electromagnet command value learning generator that includes the mathematical model for generating the command value for the excitation current comprises:

a learning function unit that evaluates the result of a run-through, which is a series of irradiation operations through the command value for the excitation current outputted from the scanning power source, updates the mathematical model based on the result of the evaluation, and accumulates experiences in the run-through; and a scanning electromagnet command value series generator that outputs to the scanning power source the command value for the excitation current to be generated, based on a latest experience accumulated by the learning function unit, by the mathematical model.

3. The particle beam irradiation apparatus according to claim 1, wherein the mathematical model generates the command value for the excitation current, based on a desired irradiation position coordinates on an irradiation subject onto which the charged particle beam is irradiated.

4. The particle beam irradiation apparatus according to claim 1, wherein the mathematical model is an inverse-map at a time when a map that has hysteresis-characteristic dynamics of the scanning electromagnet and that is to obtain an irradiation position of the charged particle beam from the command value for the excitation current is regarded as a positive map.

5. The particle beam irradiation apparatus according to claim 1, wherein the mathematical model is a feed-forward neural network.

6. The particle beam irradiation apparatus according to claim 5, wherein the feed-forward neural network has a single-layer hidden layer.

7. The particle beam irradiation apparatus according to claim 2, wherein the mathematical model generates the command value for the excitation current, based on a desired irradiation position coordinates on an irradiation subject onto which the charged particle beam is irradiated.

8. The particle beam irradiation apparatus according to claim 2, wherein the mathematical model is an inverse-map at a time when a map that has hysteresis-characteristic dynamics of the scanning electromagnet and that is to obtain an irradiation position of the charged particle beam from the command value for the excitation current is regarded as a positive map.

9. The particle beam irradiation apparatus according to claim 2, wherein the mathematical model is a feed-forward neural network.

10. The particle beam irradiation apparatus according to claim 3, wherein the mathematical model is a feed-forward neural network.

11. The particle beam irradiation apparatus according to claim 4, wherein the mathematical model is a feed-forward neural network.

12. A particle beam therapy system comprising:
a beam generation apparatus that generates a charged particle beam;
an accelerator that accelerates the charged particle beam generated by the beam generation apparatus;
a beam transport apparatus that transports a charged particle beam accelerated by the accelerator; and
a particle beam irradiation apparatus that scans, by means of a scanning electromagnet, a charged particle beam transported by the beam transport apparatus and irradiates the charged particle beam onto an irradiation subject, wherein the particle beam irradiation apparatus is a particle beam irradiation apparatus according to claim 1.

13. A particle beam therapy system comprising:
a beam generation apparatus that generates a charged particle beam;
an accelerator that accelerates the charged particle beam generated by the beam generation apparatus;
a beam transport apparatus that transports a charged particle beam accelerated by the accelerator; and
a particle beam irradiation apparatus that scans, by means of a scanning electromagnet, a charged particle beam transported by the beam transport apparatus and irradiates the charged particle beam onto an irradiation subject, wherein the particle beam irradiation apparatus is a particle beam irradiation apparatus according to claim 2.

14. A particle beam therapy system comprising:
a beam generation apparatus that generates a charged particle beam;
an accelerator that accelerates the charged particle beam generated by the beam generation apparatus;
a beam transport apparatus that transports a charged particle beam accelerated by the accelerator; and
a particle beam irradiation apparatus that scans, by means of a scanning electromagnet, a charged particle beam transported by the beam transport apparatus and irradiates the charged particle beam onto an irradiation subject, wherein the particle beam irradiation apparatus is a particle beam irradiation apparatus according to claim 3.

15. A particle beam therapy system comprising:
a beam generation apparatus that generates a charged particle beam;
an accelerator that accelerates the charged particle beam generated by the beam generation apparatus;
a beam transport apparatus that transports a charged particle beam accelerated by the accelerator; and
a particle beam irradiation apparatus that scans, by means of a scanning electromagnet, a charged particle beam transported by the beam transport apparatus and irradiates the charged particle beam onto an irradiation subject, wherein the particle beam irradiation apparatus is a particle beam irradiation apparatus according to claim 4.

16. A particle beam therapy system comprising:
a beam generation apparatus that generates a charged particle beam;
an accelerator that accelerates the charged particle beam generated by the beam generation apparatus;
a beam transport apparatus that transports a charged particle beam accelerated by the accelerator; and
a particle beam irradiation apparatus that scans, by means of a scanning electromagnet, a charged particle beam transported by the beam transport apparatus and irradiates the charged particle beam onto an irradiation subject, wherein the particle beam irradiation apparatus is a particle beam irradiation apparatus according to claim 5.

17. A particle beam therapy system comprising:
a beam generation apparatus that generates a charged particle beam;
an accelerator that accelerates the charged particle beam generated by the beam generation apparatus;

a beam transport apparatus that transports a charged particle beam accelerated by the accelerator; and a particle beam irradiation apparatus that scans, by means of a scanning electromagnet, a charged particle beam transported by the beam transport apparatus and irradiates the charged particle beam onto an irradiation subject, wherein the particle beam irradiation apparatus is a particle beam irradiation apparatus according to claim 6.

18. A particle beam therapy system comprising:

a beam generation apparatus that generates a charged particle beam;

an accelerator that accelerates the charged particle beam generated by the beam generation apparatus;

a beam transport apparatus that transports a charged particle beam accelerated by the accelerator; and a particle beam irradiation apparatus that scans, by means of a scanning electromagnet, a charged particle beam transported by the beam transport apparatus and irradiates the charged particle beam onto an irradiation subject, wherein the particle beam irradiation apparatus is a particle beam irradiation apparatus according to claim 7.

19. A particle beam therapy system comprising:

a beam generation apparatus that generates a charged particle beam;

an accelerator that accelerates the charged particle beam generated by the beam generation apparatus;

a beam transport apparatus that transports a charged particle beam accelerated by the accelerator; and a particle beam irradiation apparatus that scans, by means of a scanning electromagnet, a charged particle beam transported by the beam transport apparatus and irradiates the charged particle beam onto an irradiation subject, wherein the particle beam irradiation apparatus is a particle beam irradiation apparatus according to claim 8.

20. A particle beam therapy system comprising:

a beam generation apparatus that generates a charged particle beam;

an accelerator that accelerates the charged particle beam generated by the beam generation apparatus;

a beam transport apparatus that transports a charged particle beam accelerated by the accelerator; and a particle beam irradiation apparatus that scans, by means of a scanning electromagnet, a charged particle beam transported by the beam transport apparatus and irradiates the charged particle beam onto an irradiation subject, wherein the particle beam irradiation apparatus is a particle beam irradiation apparatus according to claim 9.

* * * * *